United States Patent [19]

Saville

[11] Patent Number: Plant 6,811

[45] Date of Patent: May 23, 1989

[54] ROSE PLANT

[75] Inventor: F. Harmon Saville, Rowley, Mass.

[73] Assignee: Nor'East Miniature Roses, Inc., Rowley, Mass.

[21] Appl. No.: 138,140

[22] Filed: Dec. 28, 1987

[51] Int. Cl.[4] ..... A01H 5/00

[52] U.S. Cl. ..... Plt./10

[58] Field of Search ..... Plt./10, 9

*Primary Examiner*—Robert E. Bagwill

*Attorney, Agent, or Firm*—Vincent G. Gioia

[57] ABSTRACT

A new unusual bright Cardinal Red miniature rose which holds its color well.

1 Drawing Sheet

The present invention relates to a new and distinct variety of rose plant of the miniature rose class, which was originated by my crossing as seed parent an unnamed, unpatented seedling of my creation and as pollen parent the variety known as "Rainbow's End" (U.S. Plant Pat. No. 5,482). The denomination of this new rose is "Savawire".

Among the novel characteristics possessed by this new variety which distinguish it from its parents and all other varieties of which I am aware are its unusual bright Cardinal Red flowers in this class of rose. Flowers hold their color well upon aging. Asexual reproduction by budding of the new variety as performed in Essex County, Mass. shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "53C" is plate 53C of The Royal Horticultural Society Colour Chart.

Parentage: Seedling.

*Seed parent.*—Unnamed seedling.

*Pollen parent.*—"Rainbow's End".

Class: Miniature.

The following observations are made of specimens grown outdoors in Essex County, Mass., during the month of October.

FLOWER

Blooming habit: Nearly continuous.

A. Bud:

(1) Size.—Small.

(2) Form.—Ovoid.

(3) Color.—As sepals divide, bud color is near Cardinal Red 53C to near Turkey red 46C. '(4) *Sepals.*—Longer than bud, slightly foliated.

(5) *Peduncle.*—Length — about $\frac{5}{8}$ inch. Aspect — straight. Strength — erect. Color — near 182B.

B. Bloom:

(1) *Size.*—Average size when fully expanded — about $\frac{7}{8}$ to 1 inch.

(2) *Borne.*—Singly, one to a stem.

(3) *Form.*—Cupped shape, becoming flat. Petals reflex and quill to points; very pronounced petal apices.

(4) *Petalage.*—Number of petals under normal conditions — about 27 to 32.

(5) *Color.*—As petals unfurl, flower coloring remains consistently in the range of near Cardinal Red 53C to Turkey Red 46C to 46D. Near white high-lights are seen at petal tips and glimpses of yellow coloring of petals toward point of petal attachment add to the attractiveness in the otherwise stable Cardinal Red flower coloring.

C. Petals:

(1) *Texture.*—Firm.

(2) *Appearance.*—Inside velvety and outside satiny.

(3) *Form.*—Broad, with pointed apices.

(4) *Arrangement.*—Regularly arranged.

(5) *Petaloids in center.*—Few.

(6) *Persistence.*—Drop off cleanly.

(7) *Fragrance.*—None.

(8) *Lasting quality.*—Very long lasting quality on plant.

REPRODUCTIVE ORGANS

A. Stamens, filaments and anthers:

*Arrangement and color.*—Regularly arranged around styles. Color — filaments near 17A.

B. Pollen:

*Color.*—Near 17A.

C. Styles: Even, medium length, thin.

D. Stigmas:

*Color.*—Near 160D.

E. Hips: None observed.

PLANT

A. Form: Compact.

B. Growth: Very vigorous, uniform branching.

*Height attained.*—About 6 to 8 inches.

C. Foliage: Compound 5 to 7 leaflets.

(1) *Size.*—Small.

(2) *Quantity.*—Abundant.

(3) *Color.*—New foliage: Upper side — near 143A. Under side — near 146D. Old foliage: Upper side — near 143A. Under side — near to 146D.

(4) *Shape.*—Oval, pointed.

(5) *Texture.*—Upper side is semiglossy; under side is matte.

(6) *Edge.*—Serrate.
(7) *Serration.*—Ordinary.
(8) *Leaf stem.*—Color — near to 185C. Under side — near 138C.
(9) *Stipules.*—Medium length, slightly bearded.
(10) *Resistance to disease.*—Blackspot — Average. Mildew — Average. Rust — Average.

D. Wood:
(1) *New wood.*—Color — near 179A. Bark — smooth.
(2) *Old wood.*—Color — near 144B. Bark — smooth.

E. Thorns:
(1) *Thorns.*—Quantity (main stalk) — ordinary. On laterals from stalk — few. Form — long, thin, slanted slightly downward. Length — short. Color — near 185A. Position — irregular.
(2) *Prickles.*—Quantity (main stalk) — few. On laterals — none.

F. Winter hardiness: Needs protection in severe climates.

I claim:

1. A new and distinct variety of rose plant of the miniature rose class and all parts thereof, substantially as shown and described, characterized particularly by attractive bright Cardinal Red flowers which hold color well upon aging.

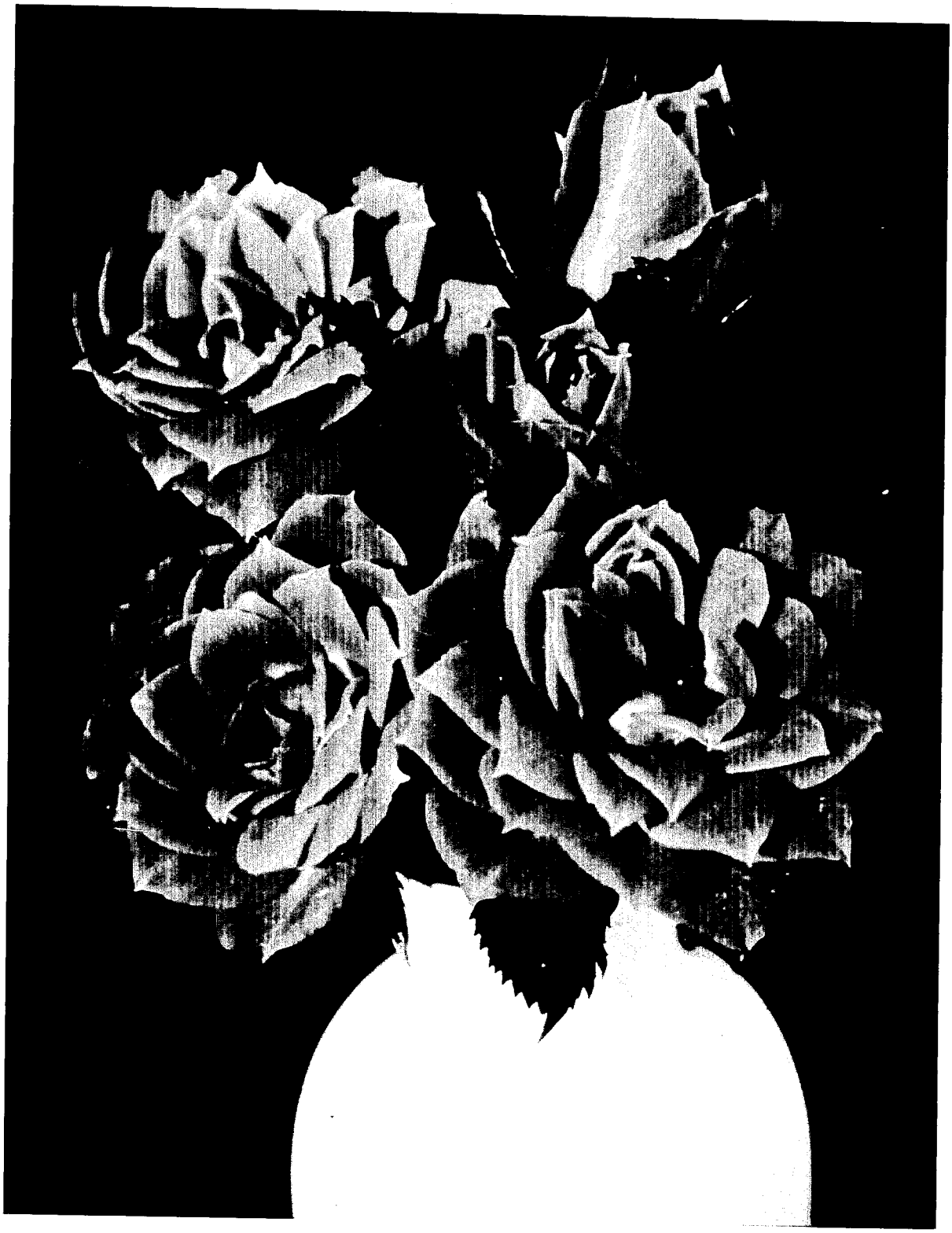

* * * * *